United States Patent [19]

Kang

[11] Patent Number: 5,846,737
[45] Date of Patent: Dec. 8, 1998

[54] CONJUGATES OF SULFORHODAMINE FLUOROPHORES WITH ENHANCED FLUORESCENCE

[75] Inventor: Hee Chol Kang, Eugene, Oreg.

[73] Assignee: Molecular Probes, Inc., Eugene, Oreg.

[21] Appl. No.: 686,858

[22] Filed: Jul. 26, 1996

[51] Int. Cl.$^6$ .................... G01N 33/533; C07K 16/00; C07D 311/88
[52] U.S. Cl. ................. 435/7.1; 435/7.5; 435/7.72; 435/7.8; 436/501; 436/544; 436/546; 436/800; 530/300; 530/387.1; 530/388.9; 530/391.3; 530/391.9; 536/23.1; 536/25.1; 536/25.2; 536/25.32; 536/26.26; 536/26.6; 536/26.7; 536/26.8; 549/229; 549/227; 549/394
[58] Field of Search .................... 549/224, 227, 549/394; 435/7.1, 7.5, 7.72, 7.8; 530/300, 387.1, 388.9, 391.3, 391.5, 391.9; 536/23.1, 25.1, 25.2, 25.32, 26.26, 26.6, 26.7, 26.8; 436/501, 544, 546, 800

[56] References Cited

U.S. PATENT DOCUMENTS

| | | |
|---|---|---|
| 4,711,955 | 12/1987 | Ward et al. . |
| 4,945,171 | 7/1990 | Haugland et al. . |
| 5,047,519 | 9/1991 | Hobbs, Jr. et al. . |
| 5,175,269 | 12/1992 | Stavrianopoulos . |
| 5,241,060 | 8/1993 | Engelhardt et al. . |
| 5,302,731 | 4/1994 | Pitner et al. . |
| 5,328,824 | 7/1994 | Ward et al. . |

OTHER PUBLICATIONS

Uehleki, A. Naturforschg. 13, 722 (1958).
Chadwick et al., Lancet, p. 412, Feb. 22, 1958.
Chen, Arch. Biochem. Biophys. 133, 263 (1969).
Bayer A.–G. Chem. Abstracts, 85, 134053h (1976).
Wittung, et al., Nature, 368, 561 (1994).
Haugland, Molecular Probes Handbook, supra, Sets 1–7 (1992).
Brinkley et al., Bioconjugate Chem., 3, 2 (1992).
Haugland et al., Meth. Mol. Biol. 45, 205 (1995).
Haugland, Meth. Mol. Biol. 45, 223 (1995).
Haugland, Meth. Mol. Biol. 45, 235 (1995).
Bioprobes 23, Molecular Probes Inc., (1996).
Bioconjugate Chem., vol. 3, pp. 2–13 (1992).

*Primary Examiner*—James O. Wilson
*Attorney, Agent, or Firm*—Allegra J. Helfenstein; Anton E. Skaugset

[57] ABSTRACT

The invention describes useful conjugates of sulforhodamine, wherein the conjugated substance and the fluorophore are separated by an alkanoic acid spacer that is attached to the fluorophore via a sulfonamide bond. The increased length of the covalent linkage due to the spacer results in dye-conjugates having a number of surprisingly advantageous properties relative to previous sulforhodamine-labeled conjugates, including increased fluorescence.

34 Claims, 5 Drawing Sheets

CONJUGATES OF SULFORHODAMINE FLUOROPHORES WITH ENHANCED FLUORESCENCE

FIELD OF THE INVENTION

The invention relates to a family of fluorescent labeled conjugates of sulforhodamines, including fluorescent conjugates of peptides, proteins, nucleotides, oligonucleotides, haptens and polysaccharides.

BACKGROUND

Fluorescent dyes are particularly suitable for biological applications in which a highly sensitive detection reagent is desirable. Fluorescent dyes are used to impart both visible color and fluorescence to other materials. Dyes that are able to preferentially bind to a specific biological ingredient in a sample enable the researcher to determine the presence or quantity of that specific ingredient. In addition, specific cellular structures can be monitored with respect to their spatial and temporal distribution in diverse environments.

The reactive dye sulforhodamine B sulfonyl chloride was described as a useful reagent for labeling proteins as early as 1958 (Uehleke, Z. NATURFORSCHG. 13, 722 (1958); Chadwick et al. LANCET, p. 412, Feb. 22, 1958; Chen, ARCH. BIOCHEM. BIOPHYS. 133 263 (1969)). Since then sulforhodamine B sulfonyl chloride (hereafter referred to as SBSC, and commercially available under the trademark LISSAMINE rhodamine B sulfonyl chloride) has been widely used to label amine-containing materials, including proteins and nucleotides. In particular, numerous protein, dextran, nucleotide and oligonucleotide conjugates of SBSC have been described, and several are commercially available. However, all lack the additional spacer present in the compounds of the present invention, whose presence has been shown to enhance the utility of the labeled nucleotides by reducing quenching effects on the fluorophores and improving utilization by enzymes that act upon the labeled probe.

The SBSC fluorophore is typically available as a mixture of isomers, as shown below:

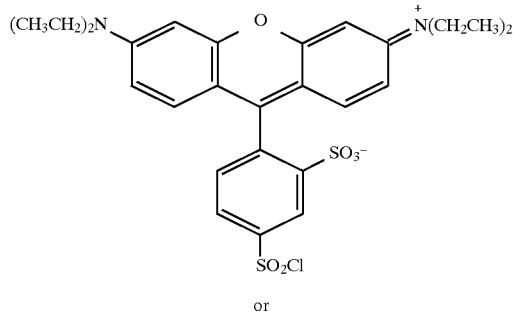

or

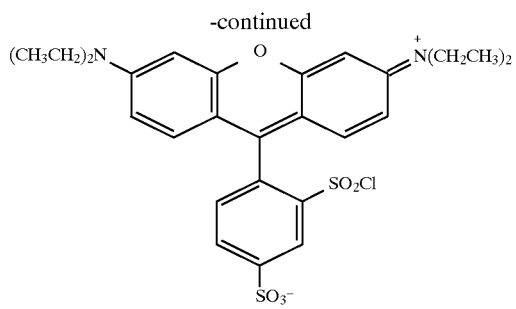

Despite the favorable characteristics of SBSC, the use of a sulfonyl chloride reactive group produces several disadvantages when it is used as a protein label. Primarily, the resulting close proximity of fluorophore to the conjugated material makes SBSC-conjugates more likely to hinder the labeled probe in biological interactions, such as with an enzyme, as when the SBSC-labeled nucleotides are used in conjunction with a nucleotide polymerase, or with a ligand binding site, as in the case of a drug receptor. Finally, the fluorescence emission of SBSC-labeled proteins tends to be quenched, relative to the fluorescence emission of the free dye.

In addition, dyes possessing a sulfonyl chloride reactive site are intrinsically very susceptible to hydrolysis by even trace amounts of water. This instability often results in labeling variability, or total labeling failure. Sulfonyl chlorides also react non-selectively with groups in proteins other than amnines, including tyrosine, histidine and serine residues. Where these residues are essential for biological activity of the proteins, this reactivity is detrimental to the use of the labeled protein. Furthermore, instability of these undesired adducts results in slow loss of the dye from the conjugates during storage.

The use of modified reactive sulforhodamine dyes allows the preparation of conjugates with a wider range of substances. In particular, conjugation can be performed using less problematic reactive groups on the fluorophore, such as succinimidyl esters.

A succinimidyl ester derivative of SBSC has been described previously (U.S. Pat. No. 5,302,731 to Pitner et al., (1994)), which was utilized to prepare a 12-amino-dodecanoic acid conjugate for use as a fluorescent pH indicator. The reactive succinimidyl ester was not described as having utility for preparing conjugates of biological polymers.

The conjugates of the present invention are more readily prepared than conjugates of SBSC, due to the hydrolytic stability of the reactive dyes used in the conjugation. The sulfonyl chloride reagents are unstable to moisture during storage, and are prone to hydrolysis in the conjugation reaction itself. This instability results in the percentage of reactive dye actually present varying between individual reactions. In addition, the reactivity of the reagent requires the use of low temperatures and relatively high pH to optimize conjugate efficiency. The conjugates of the present invention may be prepared that would not otherwise tolerate the high pH required for reaction with sulfonyl chlorides. In addition, the conjugation reaction itself can be performed in aqueous solution without the substantial loss of reactivity observed for the sulfonyl chloride.

In addition, the resulting conjugates retain or improve upon the beneficial properties of labeling with conventional sulforhodamine sulfonyl chlorides. In particular, the sulforhodamine B conjugates of the present invention exhibit fluorescence emission wavelengths that are the same or longer in wavelength than those prepared from SBSC, and thus have slightly less spectral overlap with the emission of fluorescein (as shown in FIG. 2) improving their utility for multicolor applications. Additionally, the conjugates prepared according to the present invention typically possess a higher fluorescence quantum yield than SBSC-conjugates, particularly conjugates of proteins, both as the result of permitting a higher degree of substitution and an unexpected reduction of quenching of the dyes by their conjugates (as shown in FIGS. 3 and 4). The protein-conjugates of the present invention are unexpectedly more soluble than those prepared using SBSC, and are less prone to precipitation.

SUMMARY OF THE INVENTION

The sulforhodamine conjugates of the invention possess an alkyl spacer between fluorophore and the conjugated substance. The increased length of the covalent linkage due to the alkyl spacer results in dye-conjugates having a number of surprisingly advantageous properties relative to previous sulforhodamine-labeled conjugates, including increased fluorescence. Where the conjugated substance is a member of a specific binding pair, the dye-conjugates possess utility as detection reagents for the complementary binding pair member.

DESCRIPTION OF PREFERRED EMBODIMENTS

Figure 1:
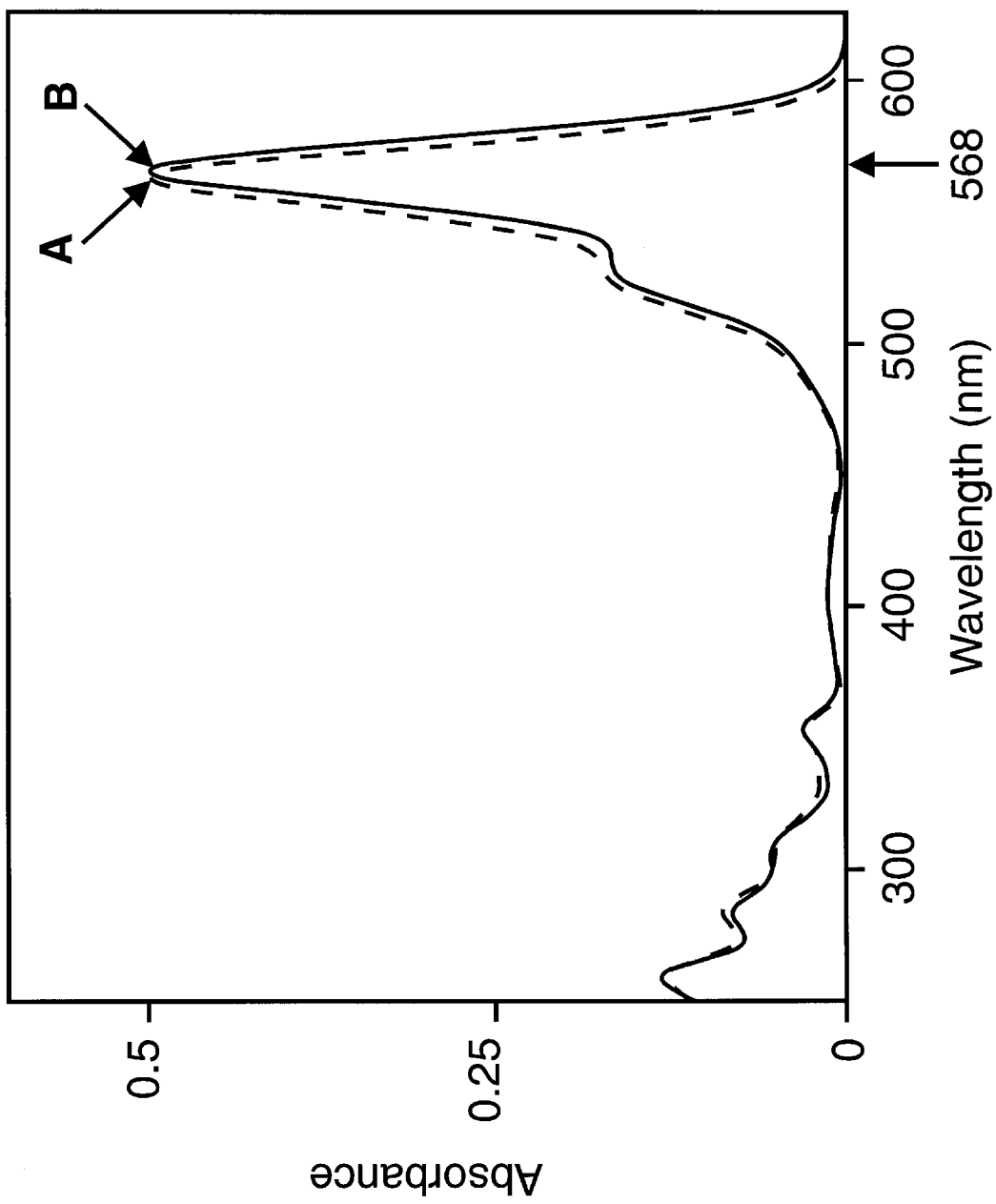
FIG. 1: The normalized absorption spectra of (A) sulforhodamine B and (B) Compound 1 dissolved in phosphate buffered saline (PBS). The arrow at 568 nm indicates that the fluorophore can be excited by the krypton-ion laser.
Figure 2:
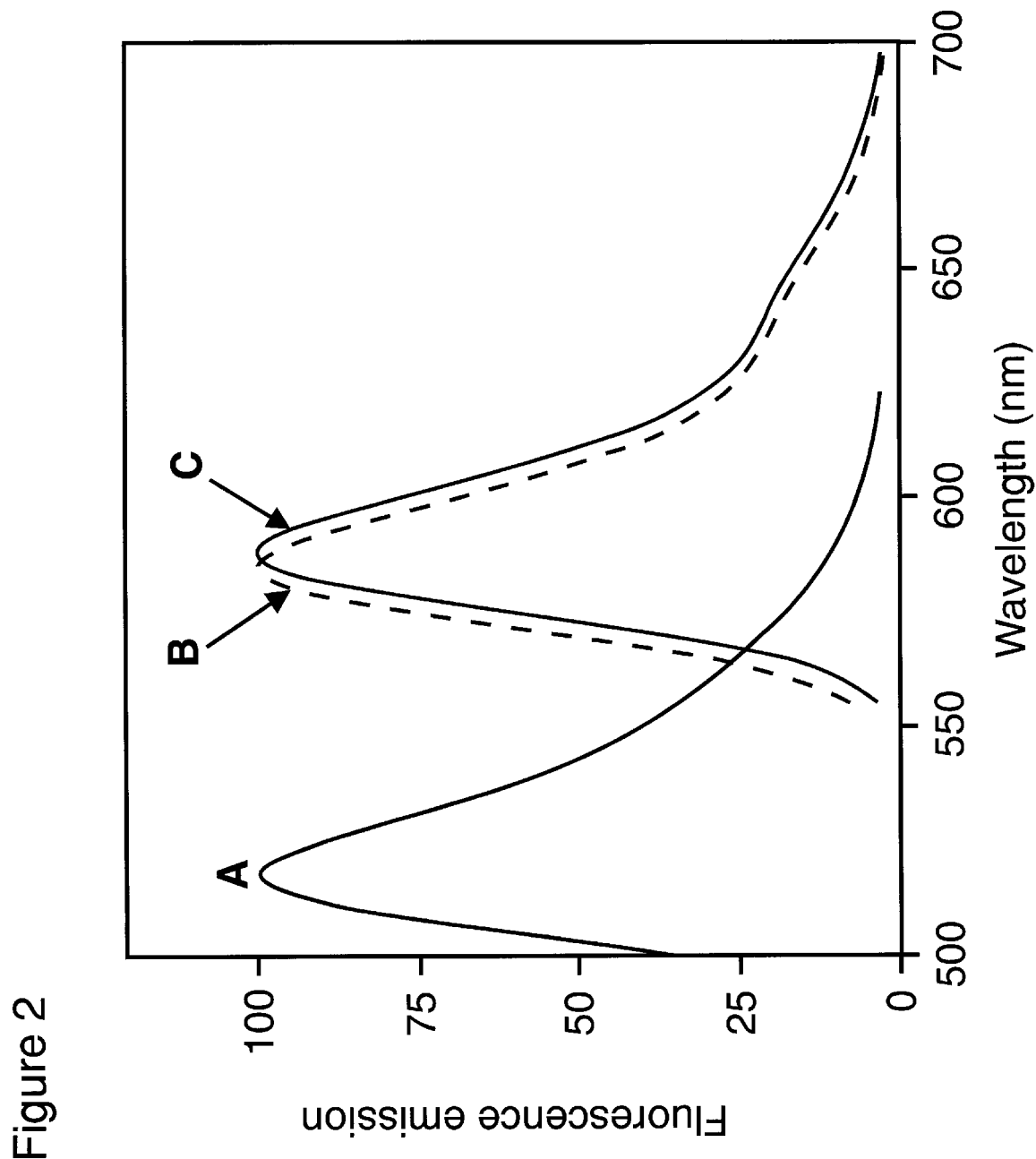
FIG. 2: The normalized emission spectra of (A) fluorescein, (B) sulforhodamine B and (C) Compound 1 dissolved in phosphate buffered saline (PBS).

The dye conjugates of the present invention are all derivatives of tetramethyl- or tetraethylsulforhodamine sulfonyl chloride. As is true for the parent sulforhodamine B sulfonyl chloride, the dye-conjugates of the invention are typically available as a mixture of the two monosulfonamide isomers possible from the reaction of an amine with the sulfonyl chloride moiety, and typically contain some disulfonamide derivative. While the two isomers are generally equivalent for many of the purposes of the present invention, purification of discrete isomers is sometimes required for the most critical assays, such as where the dye-conjugate is to be separated by a high resolution technique such as electrophoresis. While it is understood that the "para" sulfonamide isomer is typically shown and referred to, unless specifically stated otherwise, conjugates of each isomer as well as of mixtures of both isomers are encompassed by the present invention.

The dye conjugates of the present invention have the general formula

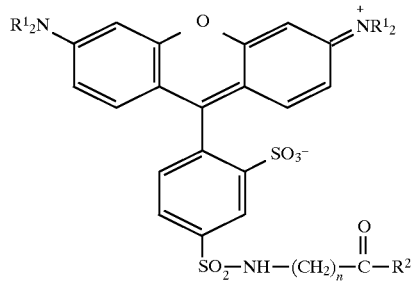

or the general formula

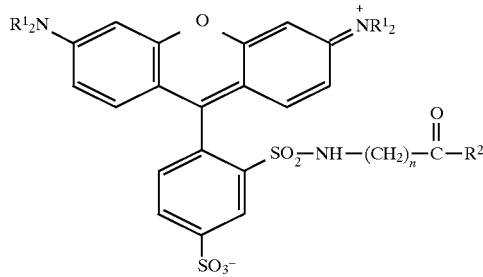

Where n=1–10. Typically n=1–7, preferably 3–5 and more preferably n=5. $R^1$ is methyl or ethyl, preferably ethyl. $R^2$ is the conjugated substance. The linkage to the conjugated substance is typically an amide, an ester or a thioester; most typically the linkage is an amide.

The starting material for synthesis of the reactive dyes used to prepare the subject conjugates is typically a sulforhodamine dye. Sulforhodamine B and its analogs, including the methyl analog (Bayer A. -G. CHEM. ABSTRACTS, 85, 134053h (1976)), are prepared by condensation of 2,4-disulfobenzaldehyde (Pfalz and Bauer) and a dialkylaminophenol (e.g. diethylaminophenol for R=$CH_2CH_3$ or dimethylaminophenol for R=$CH_3$) followed by oxidation of the dihydrorhodamine intermediate. The dye known as sulforhodamine 101, is prepared similarly from 2,4-disulfobenzaldehyde and 8-hydroxyjulolidine. Reactive derivatives and conjugates of the reaction products of sulforhodamine 101 sulfonyl chloride and aminoalkanoic acids and their advantages have been disclosed in copending patent application Ser. No. 08/485,033, which is incorporated by reference.

Sulforhodamine B or its methyl analog is first converted to a sulfonyl chloride using phosphorous oxychloride or other chlorinating agents. This reaction typically yields a mixture of the isomeric monosulfonyl chlorides accompanied by a variable amount of the disulfonyl chloride. This mixture is typically used without separation of the isomers. If desired, the isomers can be chromatographically separated following reaction with an aminoalkanoic acid. For most applications in preparing conjugates it is not necessary to separate the isomers before forming conjugates. The derivatives where R=$CH_3$ and R=$CH_2CH_3$ have similar spectra and other properties; however derivatives of sulforhodamine B are preferred for synthesis because of the commercial availability in bulk of its starting material.

The conjugates of the present invention are prepared from the sulfonyl chloride derivative of the desired sulforhodamine, generally by reaction with an omega-amino acid or its ester-protected derivative (Example 1). The resulting isomers may also be separated by chromatographic means at this step or following removal of any protecting groups (e.g. for use as a derivatization reagent in ultra-high resolution separation techniques such as gel or capillary electrophoresis); however, separation is not required or preferred. This carboxylic acid derivative is then converted to the desired reactive derivative by methods well recognized in the art, such as by conversion to a succinimidyl ester (Example 2).

Appropriate organic substances for conjugation can either be isolated from natural products, prepared synthetically, or isolated from a natural product and then synthetically modified (semi-synthetic). Amines, thiols, and alcohols are the preferred functional groups on the substance to be conjugated, as they are both more reactive and more commonly available for the modification of biomolecules. Conjugation of the intermediate reactive dye with an amine, thiol or alcohol yields an amide, thioester or ester linkage, respectively. More preferably, the sulforhodamine fluorophore is conjugated to the desired substance via an amine group on the substance, yielding an amide linkage. The dye-conjugates of the invention are prepared from either readily-available organic substances, or from initially non-reactive organic substances that have been derivatized by an appropriate functional group according to methods generally known in the art.

Typically, the conjugated substance is a poly(amino acid), polysaccharide, nucleotide, oligonucleotide or nucleic acid polymer.

In one embodiment of the invention, the conjugated substance is a heterogeneous or homogenous polymer of amino acids (a poly(amino acid)), such as a peptide or protein. While the specific demarcation line between peptides and proteins is not exact, it is typically recognized in the art that peptides have molecular weights of greater than about 1,000 daltons, and less than about 5,000 to 10,000 daltons, while proteins have molecular weights greater than about 5,000 to 10,000 daltons. Although peptides include molecules as small as dipeptides, the preferred peptides of the invention contain at least five amino acids, more preferably 5 to 36 amino acids. Preferred peptides of the invention include neuropeptides, chemotactic peptides, gastrointestinal peptides, snake toxins, protease substrates, endothelin, protein kinase substrates and others. Proteins typically possess at least secondary structure, and most often tertiary and quaternary structure. The protein conjugates of the present invention tend to be more soluble, and display less fluorescence quenching than the previously known SBSC-protein conjugates. The additional spacer in the sulforhodamine-peptide conjugates of the instant invention places the fluorophore further away from the peptide binding site, which may result in improved binding of the peptide probes to its receptor relative to the same peptide labeled with SBSC, which lacks the spacer.

The protein conjugates of the present invention encompass a variety of proteins, including but not limited to enzymes, antibodies (Example 7), lectins (Example 9), glycoproteins, lipoproteins, avidin, streptavidin (Example 7), protein A, and protein G. By enzyme is meant any of a group of catalytic proteins that are produced by living cells and that mediate and promote the chemical processes of life without themselves being altered or destroyed. Examples of appropriate enzymes suitable for conjugation include, but are not limited to, peroxidases, proteases, phosphatases, and glycosidases, such as β-D-galactosidases, and β-D-glucuronidases. Antibodies, as used herein, are any of various proteins synthesized by animals in response to the presence of a foreign substance, for example, immunoglobulin G(IgG) and its fragments, and include both polyclonal and monoclonal antibodies. Lectins, as used herein, are any of various proteins that selectively bind carbohydrates, such as cell surface carbohydrates, which can be used to identify cell type. Appropriate lectins are typically isolated from plants, such as legumes, or from bacteria, fish or invertebrates. A preferred lectin is wheat germ agglutinin. Glycoproteins, as used herein, are any of a class of proteins containing both carbohydrate and protein units. Lipoproteins, as used herein, are any of a class of proteins containing both lipid and protein units, for example LDL.

In another embodiment of the invention, the conjugated substance is a single base, single nucleoside, single nucleotide, oligonucleotide or a nucleic acid polymer. By nucleotide is meant the basic structural unit of a nucleic acid, comprising an ester of a nucleoside and one or more phosphoric acid or polyphosphoric acid groups, optionally containing an additional linker or spacer for attachment of a fluorophore or other ligand, such as an alkynyl linkage (U.S. Pat. No. 5,047,519 to Hobbs, Jr. et al., (1991), incorporated by reference) or other linkage (U.S. Pat. No. 4,711,958 to Ward et al., (1987); U.S. Pat. No. 5,175,269 to Stavrianopoulos, (1992); U.S. Pat. No. 5,241,060 to Engelhardt et al., (1993); U.S. Pat. No. 5,328,824 to Ward et al., (1994); all of which are hereby incorporated by reference). The conjugated nucleotide is typically a ribonucleotide, deoxyribonucleotide or a dideoxyribonucleotide. Preferably, the conjugated nucleotide is a mono-, di- or triphosphate ester of an adenosine, a guanosine, a uridine, a thymidine or a cytidine. More preferably, the conjugated nucleotide is uridine triphosphate or deoxyuridine triphosphate.

Oligonucleotides and nucleic acid polymers are typically large, chainlike molecules containing phosphoric acids, sugars, and purine and pyrimidine bases. Oligonucleotides are typically composed of fewer than 50 nucleotides, more typically composed of fewer than 25 nucleotides. Oligonucleotides are optionally deoxyribonucleic acid polymers (DNA) or ribonucleic acid polymers (RNA), or a hybrid thereof. Suitable oligonucleotides are optionally antisense oligonucleotides, or strands of DNA having a sequence identical to messenger RNA. DNA polymers are optionally single-stranded (ss), double-stranded (ds), triple-stranded or quadruple-stranded DNA. RNA is optionally single-stranded or double-stranded nucleic acid polymers. The nucleic acid polymer may be a natural polymer (biological in origin) or a synthetic polymer (modified or prepared artificially). The nucleic acid polymer optionally incorporates an unusual linker such as morpholine derivatized phosphates (AntiVirals, Inc., Corvallis Oreg.), or peptide nucleic acids such as N-(2-aminoethyl)glycine units (Wittung, et al., NATURE 368, 561 (1994)).

In one embodiment of the invention, the dye is attached to a nucleotide (Example 3), oligonucleotide (Example 4) or nucleic acid polymer via one or more purine or pyrimidine bases through an amide, ester, or thioester bond. In another embodiment of the invention, the dye is attached to the phosphate or carbohydrate by a bond that is an amide, ester or thioester. In yet another embodiment of the invention, the dye is attached to the conjugated substance via a phosphate, thiophosphate, phosphite, or phosphonate group through an ester or amide bond.

In one embodiment of the invention, the conjugated substance is a polysaccharide, a glycoprotein, the carbohydrate portion of a nucleotide, the carbohydrate portion of a nucleic acid polymer, or a periodate-oxidized ribonucleic acid. Where the conjugated substance is a polysaccharide, it is typically a dextran, FICOL, heparin, glycogen, amylopectin, mannan, inulin, starch, agarose and cellulose. Typically, the polysaccharide has a molecular weight of greater than 3,000, preferably greater than 10,000. All of these polysaccharides are readily available at low cost, high purity, low background absorbance and fluorescence and have relatively uniform physical properties. Where the conjugated substance is a polysaccharide, it is preferably a dextran (Example 13) or FICOL conjugate, more preferably a dextran conjugate.

One class of conjugates of the present invention includes conjugates of biologically active molecules. Biologically active molecules include, but are not limited to, drugs, toxins, metabolites, pesticides, pollutants and the like. In one embodiment of the invention, the conjugated substance is a drug or toxin. Where the conjugated substance is a drug, preferred drugs of interest are the alkaloids (including morphine alkaloids), steroids, lactams having from 5 to 6 annular members, aminoalkylbenzenes, benzheterocyclics, purines, marijuana-derived drugs, vitamins, prostaglandins, antibiotics and aminoglycosides, as well as their individual derivatives and metabolites. Metabolites related to diseased states include spermine, galactose, phenylpyruvic acid and porphyrin Type 1. Among pesticides of interest are polyhalogenated biphenyls, phosphate esters, thiophosphates, carbamates, polyhalogenated sulfenamides, their metabolites and derivatives.

In another embodiment of the invention, the conjugates of the present invention are conjugates of a member of a specific binding pair, such as an antigen or hapten, such as biotin, digoxigenin, tyramine or psoralen. Typically, where the conjugated substance is a hapten, the hapten has a molecular weight less than 1,000.

Alternatively, the conjugates of the present invention are conjugates of cellular systems, cellular fragments, or subcellular particles such as mitochondrial particles or isolated nuclei. Examples of this type of conjugated material include virus particles, bacterial particles, virus components, and biological cells (Example 10).

In one aspect of the invention, the dye-conjugate contains a single fluorophore per conjugated substance. Typically, conjugates of small (i.e. low molecular weight) molecules are labeled with a single sulforhodamine fluorophore. Conjugates of most low molecular weight drugs, peptides, toxins, nucleotides and other organic molecules are prepared by organic synthesis methods using the reactive dyes of the invention, by means well recognized in the art (Haugland, MOLECULAR PROBES HANDBOOK, supra, Sets 1–7, (1992)). Preferably, conjugation to form a covalent bond consists of simply mixing the reactive dyes of the present invention in a suitable solvent in which both the reactive dye and the substance to be conjugated are soluble. The reaction preferably proceeds spontaneously without added reagents at room temperature or below. Chemical modification of water-insoluble substances, so that a desired dye-conjugate may be prepared, is preferably performed in an aprotic solvent such as dimethylformamide, dimethylsulfoxide, acetonitrile, acetone, ethyl acetate, toluene, or chloroform. Similar modification of water-soluble materials is readily accomplished through the use of appropriate reactive dyes to make them more readily soluble in organic solvents.

In another aspect of the invention, the conjugated substance contains more than one fluorophore per conjugated substance. Typically, conjugated polymers of biomolecules (i.e. biopolymers) possess more than one conjugated sulforhodamine fluorophore. Alternatively, where the resulting dye-conjugate will be utilized in a fluorescence polarization assay, the preferred dye-conjugates will have an average degree of substitution of less than or equal to one fluorophore per biomolecule.

Conjugates of biopolymers, including proteins, polysaccharides and oligonucleotides are typically prepared by means well recognized in the art (for example, Brinkley et al., BIOCONJUGATE CHEM., 3, 2 (1992); Haugland et al., METH. MOL. BIOL. 45, 205 (1995); Haugland, METH. MOL. BIOL. 45, 223 (1995); Haugland, METH. MOL. BIOL. 45, 235 (1995); BIOPROBES 23, Molecular Probes Inc., (1996)). Preferred reactive sites are aliphatic amine residues, although other nucleophiles such as alcohols, thiols, phenols, phosphates or others may also be useful provided they form sufficiently stable dye-conjugates.

When modifying biopolymers with the dyes, an excess of dye is typically used, relative to the expected degree of dye substitution. Any residual, unreacted dye or a dye hydrolysis product, is typically removed by dialysis, chromatography or precipitation (Example 7). Presence of residual, unconjugated dye can be detected by thin layer chromatography using a solvent that elutes the dye but not its biopolymer conjugate. In all cases it is usually preferred that the reagents be kept as concentrated as practical so as to obtain adequate rates of conjugation. When the substance to be conjugated is a protein, the preferred protein concentration is 1 to 10 mg/mL. Modifications of the nucleotides, oligonucleotides and nucleic acids may require preconversion of these species to amines by methods recognized in the art (For example, as described in Hobbs, Jr. et al., (1991), Ward et al., (1987), Stavrianopoulos, (1992), Engelhardt et al., (1993) or Ward et al., (1994), supra).

For soluble dye-conjugates that have multiple attachment sites, the degree of substitution of the biopolymer is typically determined by first dissolving the dye-free unlabeled biopolymer in a suitable solvent, and measuring its long wavelength absorption. A determination of the long-wavelength absorption of the labeled dye-conjugate can then be used to determine the approximate degree of substitution of the conjugate, given an approximate value for the extinction coefficient of the sulforhodamine B fluorophore. The value that is typically used for the extinction coefficient for the dyes of the present invention for this calculation is 120,000 $cm^{-1}M^{-1}$.

In one aspect of the invention, the conjugate of the invention is associated with an additional substance, that binds to either the sulforhodamine fluorophore or the conjugated substance through noncovalent interaction to form a complex. In a specific embodiment, the additional substance is an antibody, a lectin, a receptor, an oligonucleotide, a nucleic acid, or a polymer. The additional substance is optionally used to probe for the location of the dye-conjugate, for example, as a means of enhancing or quenching the signal of the dye-conjugate. Of particular utility is the binding of an anti-tetramethylrhodamine antibody to the sulforhodamine fluorophore, as antitetramethylrhodamine recognizes the sulforhodamine fluorophores of the present invention (Example 18), and is commercially available. For example, a labeled anti-tetramethylrhodamine antibody can be used to amplify the initial signal resulting from the sulforhodamine fluorophore itself.

In another embodiment of the invention, a reactive sulforhodamine dye having a alkanoic acid spacer, preferably a succinimidyl ester derivative (Example 2) is provided with instructions for conjugating the dye to a substance possessing an appropriate functional group, and optionally for recovering or purifying the materials labeled thereby. This combination of reactive dye and instructions therefore comprise a kit for labeling a specific substance. In selected embodiments of the invention, the kit thereby formed would possess utility for labeling peptides, proteins, polysaccharides, nucleotides, oligonucleotides or nucleic acid polymers. The dye-conjugates of the present invention are well-suited for preparation using such a kit, as the reactive dyes used possess greatly enhanced stability with respect to SBSC, and can therefore more readily be shipped and stored without loss of reactivity.

Applications of the Dye-Conjugates

Typically, the dye-conjugate is a labeled member of a specific binding pair, and is used as a fluorescent probe for the complementary member of that specific binding pair. A specific binding pair member can be a ligand or a receptor. As used in this document, the term ligand means any organic compound for which a receptor naturally exists or can be prepared. A receptor is any compound or composition capable of recognizing a spatial or polar organization of a molecule, e.g. epitopic or determinant site. Ligands for which naturally occurring receptors exist include natural and synthetic proteins, including avidin and streptavidin, antibodies, enzymes, and hormones; nucleotides and natural or synthetic oligonucleotides, including primers for RNA and single- and double-stranded DNA; polysaccharides and carbohydrates. Ligands and receptors are complementary members of a specific binding pair, each specific binding pair member having an area on the surface or in a cavity that specifically binds to and is complementary with a particular spatial and polar organization of the other. Representative specific binding pairs are shown in Table 1.

TABLE 1

Representative Specific Binding Pairs

| | |
|---|---|
| antigen | antibody |
| biotin | avidin (or streptavidin) |
| IgG* | protein A or protein G |
| drug receptor | drug |
| toxin receptor | toxin |
| carbohydrate | lectin |
| peptide receptor | peptide |
| protein receptor | protein |
| carbohydrate receptor | carbohydrate |
| DNA (RNA) | aDNA (aRNA)† |
| enzyme | substrate |

*IgG is an immunoglobulin
†aDNA and aRNA are the antisense (complementary) strands used for hybridization In one aspect of the invention, the specific binding pair member is an antibody or antibody fragment, avidin or streptavidin. In this embodiment of the invention, the complementary binding pair member is typically a hapten, an antigen or a biotin. Where the complementary binding pair member is a hapten, the hapten typically has a molecular weight less than 1,000. In another aspect of the invention, the specific binding pair member is an oligonucleotide or nucleic acid polymer. Optionally, the complementary binding pair member is present in a cell, bacteria, virus or yeast cell such as an Fc receptor (Example 19). Alternatively, the complementary member is immobilized on a solid or semi-solid surface, such as a polymer, polymeric membrane (such as polyvinylidene difluoride or nitrocellulose) or polymeric particle (such as a microsphere), or in a semi-solid matrix (such as an electrophoretic gel).

Preferably, the fluorescent conjugate of a specific binding pair member is useful for detecting and optionally quantifying the presence of the complementary specific binding pair member in a sample, by methods that are well known in the art. Typically, the fluorescently labeled specific binding pair member is added to a sample that contains, or is thought to contain, the complementary specific binding pair member. Sufficient time is allowed for the two members of the specific binding pair to form a complex, the nature of said complex being dependent upon the type of specific binding pair utilized, but is typically characterized as non-covalent (i.e. Van der Waals and ionic) interaction. After sufficient time has elapsed, the sample is observed for a colorimetric or fluorescent signal to indicate localization of the fluorescent conjugate. Detection of the complex is typically facilitated by washing or rinsing the sample to remove uncomplexed dye-conjugate. The sulforhodamine conjugate of the present invention is optionally combined with conjugates of other fluorophores that exhibit detectably distinct fluorescence, so as to detect multiple targets.

Alternatively, multiple specific binding pair members may be sequentially linked to the dye-conjugate, the complementary member, or to both, resulting in a series of specific binding pairs interposed between the fluorophore and the substance of interest. In one embodiment of the invention, a series of labeled specific binding pair members is used to amplify the labeling of the analyte of interest. Table 2 shows the representative examples of specific binding complexes with and without additional specific binding pairs interposed between the sulforhodamine fluorophore and the analyte.

TABLE 2

Representative Specific Binding Complexes

| ANALYTE | ADDITIONAL PAIRS | | | COMPLEMENTARY CONJUGATE |
|---|---|---|---|---|
| DNA | aDNA--biotin | avidin | | biotin--enzyme |
| DNA | aDNA--antigen | antibody--biotin | avidin | biotin--enzyme |
| DNA | | | | aDNA--enzyme |
| DNA | aDNA--biotin | | | avidin--enzyme |
| DNA | aDNA--hapten* | | | anti-hapten--enzyme |
| RNA | aRNA--hapten* | | | anti-hapten--enzyme |
| RNA | aDNA--biotin | | | avidin--enzyme |
| antigen | mouse antibody | anti-mouse--biotin | | avidin--enzyme |
| antigen | mouse antibody | anti-mouse | mouse anti-enzyme | enzyme |
| antigen | | | | antibody--enzyme |

TABLE 2-continued

Representative Specific Binding Complexes

| ANALYTE | ADDITIONAL PAIRS | COMPLEMENTARY CONJUGATE |
|---|---|---|
| antigen | antibody--hapten* | anti-hapten--enzyme |
| carbohydrate | lectin--biotin | avidin--enzyme |
| receptor‡ | ligand--biotin | anti-biotin--enzyme |
| IgG | protein A--hapten* | anti-hapten--enzyme |

‡ for instance a drug receptor, a toxin receptor, peptide receptor, protein receptor or carbohydrate receptor
-- is a covalent bond between two reagents; all other bonds are noncovalent While the resulting complex is detectable colorimetrically, using ambient light, typically the complex is detected by the fluorescence properties of the labeled specific binding pair member. Upon illumination, such as by an ultraviolet or visible wavelength emission lamp, an arc lamp, a laser, or even sunlight or ordinary room light, the labeled conjugates and specific binding pair complexes display intense visible absorption as well as fluorescence emission. Selected equipment that is useful for illuminating the dye-conjugates of the invention includes, but is not limited to, hand-held ultraviolet lamps, mercury arc lamps, xenon lamps, argon-ion lasers, krypton-ion lasers and YAG lasers. A krypton-ion laser, which provides illumination at 568 nm, is a preferred excitation source. These illumination sources are optionally integrated into laser scanners, fluorescence microplate readers, standard or minifluorometers, or chromatographic detectors. This colorimetric absorbance or fluorescence emission is optionally detected by visual inspection, or by use of any of the following: CCD cameras, video cameras, photographic film, laser scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, a fluorescence microscope or a fluorometer, the instrument is optionally used to distinguish and discriminate between the dye-conjugate and a second fluorophore with detectably different optical properties, preferably, by distinguishing the fluorescence response of the dye-conjugate from that of the second fluorophore. Additional fluorophores may also be detected. Where the sample is examined using a flow cytometer, examination of the sample optionally includes sorting the specific binding pair complex based on the fluorescence response of the dye-conjugate.

It is also possible to utilize the dyes to label reactive sites such as occur at the surface of cells, in cell membranes or in intracellular compartments such as organelles, or in the cell's cytoplasm.

In addition to their utility as labeled specific binding pair members, the conjugates of the present invention can also be used for a variety of other purposes, including any purposes that have been described for conjugates of SBSC or sulforhodamine 101 sulfonyl chloride. Primary applications include use of conjugates in immunofluorescence, fluorescence in situ hybridization, probing of receptors with a low or high molecular weight fluorescent analogs, microinjection into cells, and the tracing of labeled cells or polymers. The deoxyribonucleotide conjugates of the present invention are readily incorporated into nucleic acids by DNA polymerase and can be used for in situ hybridization or other techniques (Example 16).

The examples below are given so as to illustrate the practice of this invention. They are not intended to limit or define the entire scope of this invention.

EXAMPLES

Example 1

Preparation of 6-(4-(and 2-)-(9-(3,6-bis(diethylamino)) xanthylium)-3-(and 5-)-sulfo-1-phenylsulfonamido) hexanoic acid (Compound 1):

The following mixture of compounds is prepared:

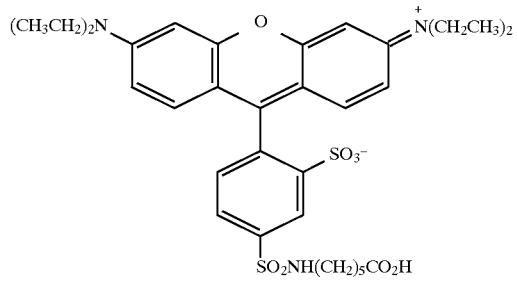

and

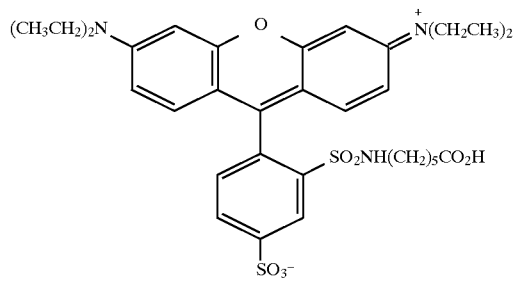

To a solution of 0.32 g (1.77 mmol) of methyl 6-aminohexanoate hydrochloride and 0.5 mL of triethylamine in 50 mL of chloroform is added 0.70 g (1.21 mmol) of sulforhodamine B sulfonyl chloride (SBSC) in small portions over a period of 10 minutes while the reaction mixture is stirred at 0° C. After the reaction mixture is stirred at room temperature 15 hours, it is washed with three 50 mL portions of water. The organic layer is separated, dried over anhydrous sodium sulfate and concentrated under reduced pressure to give a dark purple solid. This crude methyl ester derivative is purified by chromatography on silica gel with 2.5% methanol in chloroform as eluant to give 0.57 g (69%) of the methyl ester.

To a suspension of 0.55 g (1.09 mmol) of the above methyl ester in 10 mL of dioxane is added 20 mL of 6M HCl dropwise over a period of 5 minutes. After the reaction mixture is stirred at room temperature for 18 hours, it is poured into 200 mL of water. The resulting solid is collected by filtration and purified by chromatography on silica gel with 7% methanol in chloroform as eluant. A dark purple solid (355 mg, 66%) is obtained as a mixture of two isomers. TLC: $R_f$=0.37 (silica gel, 20% methanol in chloroform). $^1$H NMR (DMSO-d$_6$): δ=8.40 (s, 1H, ArH), 7.96–7.85 (m, 2H, 2×ArH), 7.47 (d, 1H, ArH), 7.08–7.02 (m, 2H, 2×ArH), 6.98 (d, 1H, ArH), 6.93 (s, 2H, 2×ArH), 3.73–3.60 (q, 8H, 4×CH$_2$), 2.90–2.83 (m, 2H, CH$_2$), 2.19–2.11 (m, 2H, CH$_2$), 1.50–1.40 (m, 4H, 2×CH$_2$), 1.30–1.26 (m, 2H, CH$_2$), 1.25 (t, 12H, 4×CH$_3$). Absorption maximum: 570 nm (ε=114,900 cm$^{-1}$M$^{-1}$) in pH 7.5 phosphate buffer, emission maximum: 590 nm in pH 7.5 phosphate buffer solution. High resolution FAB-MS m/e (M+H): calcd 672.2416; found 672.2417.

Example 2

Preparation of succinimidyl 6-(4-(and 2-)-(9-(3,6-bis (diethylamino))xanthylium)-3-(and 5-)-sulfo-1-phenylsulfonamido)hexanoate (Compound 2):

The following mixture of compounds is prepared:

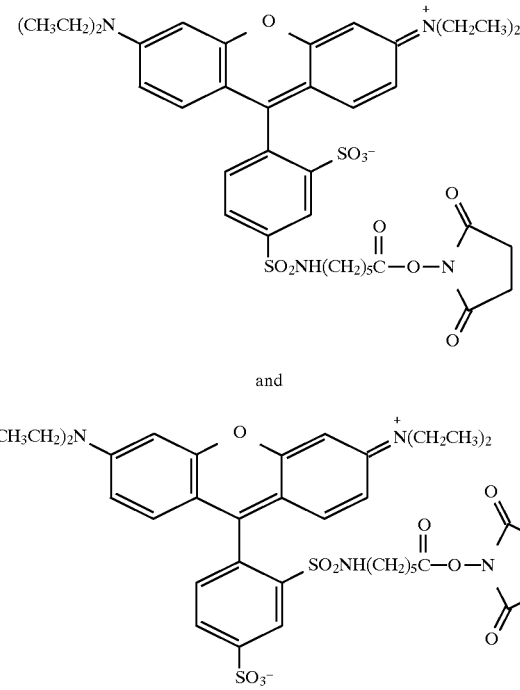

To a solution of 350 mg (0.52 mmol) of Compound 1 (Example 1) in 7 mL of DMF is added 200 μL (1.43 mmol) of triethylamine, followed by addition of 200 mg (0.60 mmol) of O-(N-succinimidyl)-N,N,N',N'-tetramethyluronium tetrafluoroborate. After the reaction mixture is stirred at room temperature for 5 hours, it is diluted with 100 mL of chloroform, washed with water, dried over anhydrous sodium sulfate and concentrated under reduced pressure to give a solid. This solid is dissolved in 10 mL of chloroform. The resulting solution is added dropwise into 100 mL of ether while stirring vigorously at room temperature. The resulting precipitate is collected by filtration and dried under vacuum to give 295 mg (74%) of a purple solid as mixed isomers. TLC: $R_f$=0.36 (silica gel, 15% methanol in chloroform; $^1$H NMR (DMSO-d$_6$): δ=8.41 (s, 1H, ArH), 7.96–7.88 (m, 2H, 2×ArH), 7.48 (d, 1H, ArH), 7.07–7.01 (m, 2H, 2×ArH), 6.99 (d, 1H, ArH), 6.96 (s, 2H, 2×ArH), 3.70–3.57 (q, 8H, 4×CH$_2$), 2.89–2.81 (m, 2H, CH$_2$), 2.80 (s, 4H, 2×CH$_2$), 2.69–2.63 (m, 2H, CH$_2$), 1.70–1.49 (m, 2H, CH$_2$), 1.52–1.35 (m, 4H, 2×CH$_2$), 1.20 (t, 12H, 4×CH$_3$). Absorption maximum: 560 nm (ε=126,000 cm$^{-1}$M$^{-1}$) in methanol; emission maximum: 580 nm in methanol. High resolution PAB-MS m/e (M+H): calcd 769.2580; found 769.2579.

Example 3

Preparation of a nucleotide conjugate of sulforhodamine (Compound 3):

To a solution of 2 mg of 5-(3-aminoallyl)-2'-deoxyuridine-5'-triphosphate, ammonium salt (Sigma Chemical) in 300 μL of water is added a solution of 4 mg of Compound 2 (Example 2) in 150 μL of DMF, followed by addition of 5 μL of triethylamine. After the mixture is stirred at room temperature for 3 hours, it is purified by chromatography over lipophilic SEPHADEX resin using water for elution. The desired fractions are combined and lyophilized to give the fluorescent nucleotide conjugate as a dark red solid.

Example 4

Preparation of an oligonucleotide conjugate of sulforhodamine (Compound 4):

A sample of 500 μg of a 5'-amine modified, 24-base M13 primer sequence is dissolved in 220 μL of 0.1M borated sodium bicarbonate pH 8.5 aqueous buffer in the microcentrifuge tube. To this oligonucleotide solution is added a solution of 1 mg of Compound 2 (Example 2) in 35 μL of DMF. The reaction mixture is shaken by hand for a few minutes and allowed to stand at room temperature for 16 hours. To the mixture is added 15 μL of 5M NaCl and 3 volumes of cold 100% ethanol. The resulting mixture is incubated at −20° C. for 30–60 minutes, and then microcentrifuged for 15–30 minutes at 4° C. (5,000–10,000 g). After microcentrifugation, the ethanol supernate is decanted, and the pellet is resuspended in 100 μL H$_2$O. The labeled oligonucleotide is then purified by HPLC on a 220 mm×10 mm 300 Å C8 reverse phase column (Rainin Instrument Co., Woburn, Mass.) using the following gradient: Solvent a—0.1M TEAA (pH ~7), Solvent B—acetonitrile. Ramp Solvent B from 15% to 60% over 30 minutes. Detection is accomplished using a Waters 490 dual wavelength UV-Vis detector monitoring 254 nm and 560 nm. The desired peak is collected and evaporated to yield the fluorescent oligonucleotide.

Example 5

Preparation of a phalloidin conjugate (Compound 5):

To a solution of 3 mg of aminophalloidin p-toluenesulfonate and 4 mg of Compound 2 (Example 2) in 300 μL of DMF is added 5 μL of triethylamine and the mixture is stirred at room temperature for 1 hour. To the reaction mixture is added 7 mL of ether and the resulting precipitate is collected by centrifugation. The crude product is purified by chromatography over lipophilic SEPHADEX resin using water for elution. The desired fractions are combined and lyophilized to give the fluorescent phalloidin conjugate as a dark purple solid.

Example 6

Preparation of a biocytin conjugate of sulforhodamine (Compound 6):

Biocytin (Molecular Probes, Inc., Eugene, Oreg.) (74.4 mg, 0.2 mmol) and 8 mg NaOH are dissolved in 1 mL water. To the resulting clear solution is added 125 mg (0.2 mmol) Compound 2 dissolved in 1 mL dimethylformamide. After 2 hours at room temperature the solution is diluted with 50 mL water and acidified with 1 mL of 1M HCl. The resulting product is collected by centrifugation, washed well with water and dried. The biocytin-dye conjugate is purified by chromatography on silica gel using mixtures of chloroform and methanol for elution. The pure conjugate is characterized by the formation of a fluorescent complex when the conjugate is treated with excess avidin. The resulting complex comigrates with unlabeled avidin on a SEPHADEX G 100 resin filtration column.

Example 7

Protein conjugates of sulforhodamine:

Protein conjugates of sulforhodamine B are prepared using Compound 2 (Example 2). The degree of substitution achieved on the selected proteins (goat anti-mouse IgG (GAM) or streptavidin (STR)) is then determined.

A fresh solution of the desired protein is prepared that is 10 mg protein/mL in 0.1M sodium bicarbonate. The labeling reagent (Compound 2) is dissolved in DMF to give a concentration of 10 mg dye/mL. Predetermined amounts of the labeling reagent in DMF are slowly added to the protein solution with stirring. A molar ratio of 10 equivalents dye to equivalent of protein is typical, though the optimal amount varies with particular labeling reagent and protein being labeled. The reaction mixture is incubated at room temperature for one hour. The dye-protein conjugate is separated from free unreacted reagent by gel filtration on a CEL-LUFINE GH-25 column equilibrated in PBS. The initial, protein-containing colored band is collected from the column, and the degree of substitution is determined by measuring the absorbance of the conjugate at 575 nm, and calculating the degree of substitution using an extinction coefficient of 120,000 $cm^{-1}M^{-1}$ for the dye.

Dye conjugates are similarly prepared using SBSC except that the protein solution is maintained at pH 9, and the labeling reaction is conducted at ice bath temperatures to minimize hydrolysis of the labeling reagent.

The advantageous preparation of the dye-conjugates of the present invention are demonstrated by the following comparison of labeling efficiency of Compound 2 as compared to SBSC, as determined by preparing conjugates of streptavidin with different dye-to-protein ratios:

| Protein | Dye:Protein Ratio | Fluorophores/Protein (mole/mole) | |
| --- | --- | --- | --- |
| | | SBSC | Compound 2 |
| streptavidin | 3 | 0.8 | 2.4 |
| streptavidin | 5 | 1.2 | 3.5 |
| streptavidin | 7 | 1.4 | 4.9 |
| streptavidin | 10 | 1.8 | 5.7 |
| streptavidin | 15 | 2.2 | 5.8 |

As shown above, the conjugates of the present invention exhibit a greater degree of dye incorporation into the protein at similar molar ratios of reactive dye to protein.

Example 8

Figure 3:
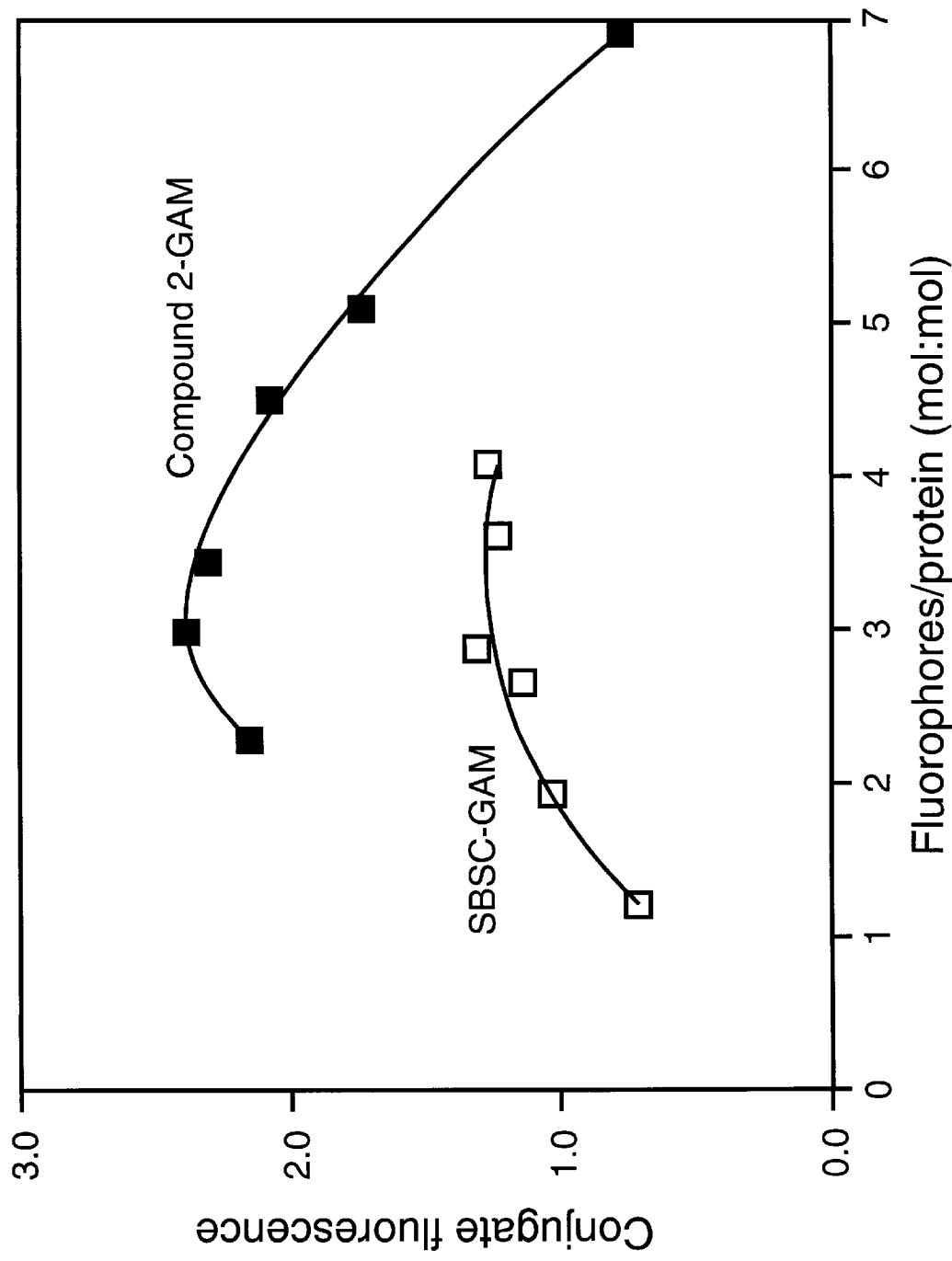
FIG. 3: Total fluorescence of a goat anti-mouse conjugate of the invention (Compound 2-GAM) vs. a goat anti-mouse conjugate of sulforhodamine B sulfonyl chloride (SBSC-GAM), plotted as a function of the degree of substitution of the conjugate, as described in Example 8.
Figure 4:
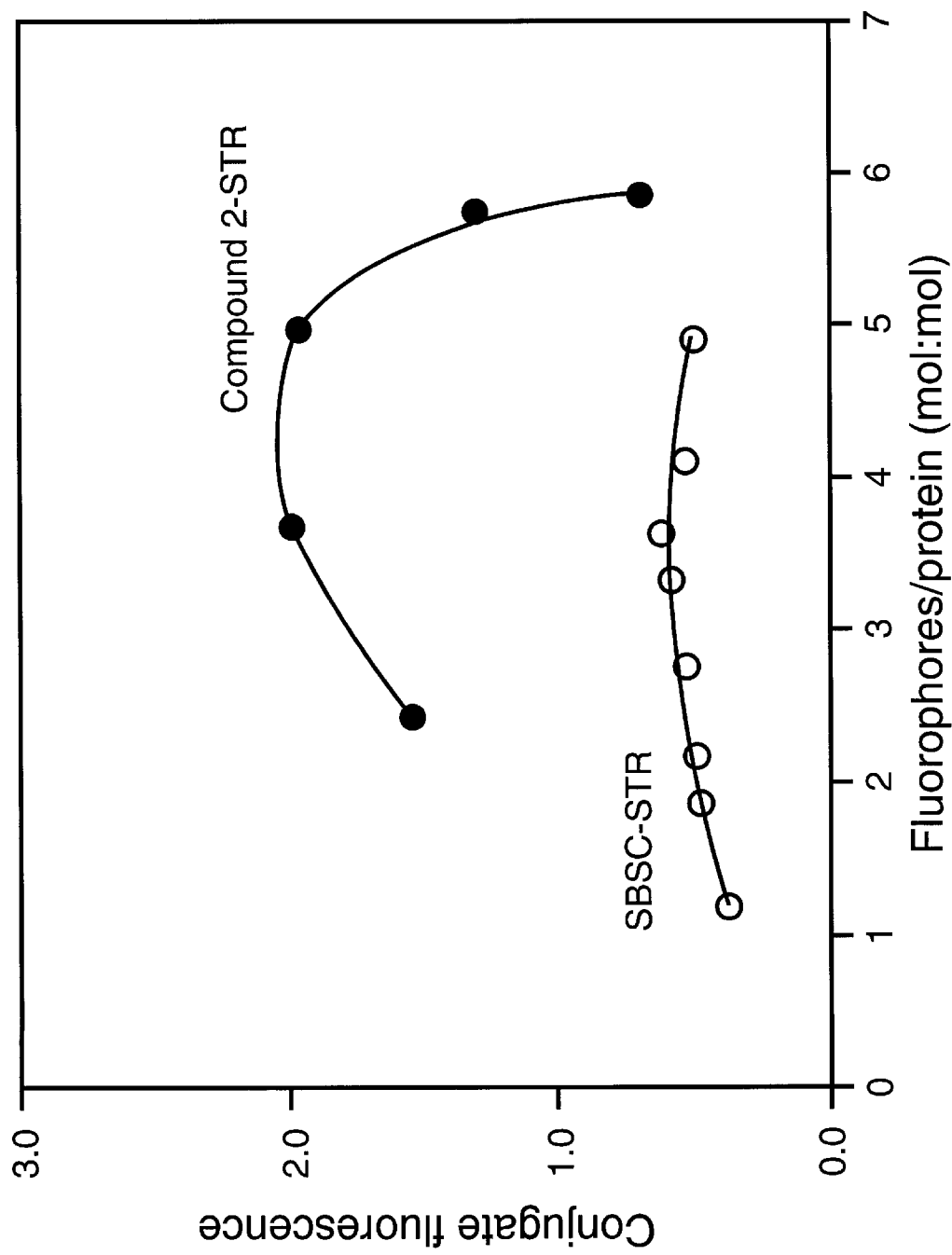
FIG. 4: Total fluorescence of streptavidin conjugates of the invention (Compound 2-STR) vs. a streptavidin conjugate of sulforhodamine B sulfonyl chloride (SBSC-STR), plotted as a function of the degree of substitution of the conjugate, as described in Example 8.

Total fluorescence of selected dye conjugates as a function of degree of substitution:

The total fluorescence of selected conjugates of the dyes of the present invention is plotted against the degree of substitution of the conjugate. Total fluorescence is the product of the degree of substitution and the quantum yield, relative to a common standard (in this case, sulforhodamine B). The degree of substitution is determined as described earlier (Example 7). The resulting dependence of fluorescence on degree of substitution is shown for goat anti-mouse and streptavidin conjugates in FIGS. 3 and 4. As shown, as the degree of substitution increases, the total fluorescence increases, until the point at which the quantum yield begins to decrease due to crowding of the dye molecules and the resultant fluorescence quenching, thereby canceling the effect of additional dye substitution.

Example 9

Preparation of a lectin conjugate of sulforhodamine:

Wheat germ agglutinin (WGA) is dissolved at 10 mg/mL in 0.1M sodium bicarbonate pH 8.3, containing N-acetylglucosamine at a reagent-to-protein ratio of 15. The addition of N-acetylglucosamine is necessary to protect the active site of the lectin from reacting with the dye during the conjugation reaction. Compound 2 is dissolved at 10 mg/mL in DMF and added to the WGA solution at a dye-to-protein molar ratio of 5, and the solution is stirred for 1 hour at room temperature. Similarly, a solution of WGA in bicarbonate at pH 9.0 is treated with SBSC at an increased dye-to-protein ratio of 15. Both reactions are terminated by the addition of hydroxylamine to reach a final concentration of 0.1M, and the resulting conjugates are purified using size exclusion chromatography as described in Example 7. Both reactions produce conjugates having a degree of substitution of approximately 1.1, and both conjugates exhibit a similar activity for binding to Gram-positive bacteria, such as Bacillus and Staphylococcus (Example 17).

Example 10

Preparation of a bacterial conjugate of sulforhodamine:

Freshly cultured bacteria are washed with water, then boiled in water for 45 minutes. The heat-killed bacteria ($5 \times 10^8$/mL) are labeled with Compound 2 (30 µg/mL) in 0.15M bicarbonate buffer, pH 8.6 at room temperature for 60 minutes with constant stirring. The free dye is removed by washing three times with phosphate buffered saline (PBS), pH 7.4. The resulting labeled bacteria exhibit red fluorescence.

Example 11

Utility of streptavidin conjugate of sulforhodamine:

The efficacy of a streptavidin conjugate of Compound 2 (prepared as described in Example 7) is tested in parallel with a streptavidin conjugate of SBSC. The comparison is performed using a test to detect antinuclear antibodies commercially available from INOVA Diagnostics Inc. (San Diego, Calif.). The commercial assay consists of a series of fixed cells on slides, and an autoimmune serum against cell nuclei. The streptavidin conjugate of Compound 2 exhibits a degree of substitution of 2.4 moles of dye per mole of protein, while the streptavidin conjugate of SBSC exhibits a degree of substitution of 2.2 dyes per mole. The cell nuclei are treated with either positive serum or negative serum (as a control), and are then developed with biotinylated protein A (Molecular Probes, Inc., Eugene Oreg.). The streptavidin conjugates above are then used to label the treated cells at a concentration of 5 µg/mL. The Compound 2 streptavidin conjugate yields brighter nuclear staining and lower fluorescence background than the conjugate prepared using SBSC (approximately two-fold more fluorescent, as measured using a fluorescent microscope coupled to a Photometrics Star-I cooled CCD camera for quantitative digital imaging).

Example 12

Figure 5:
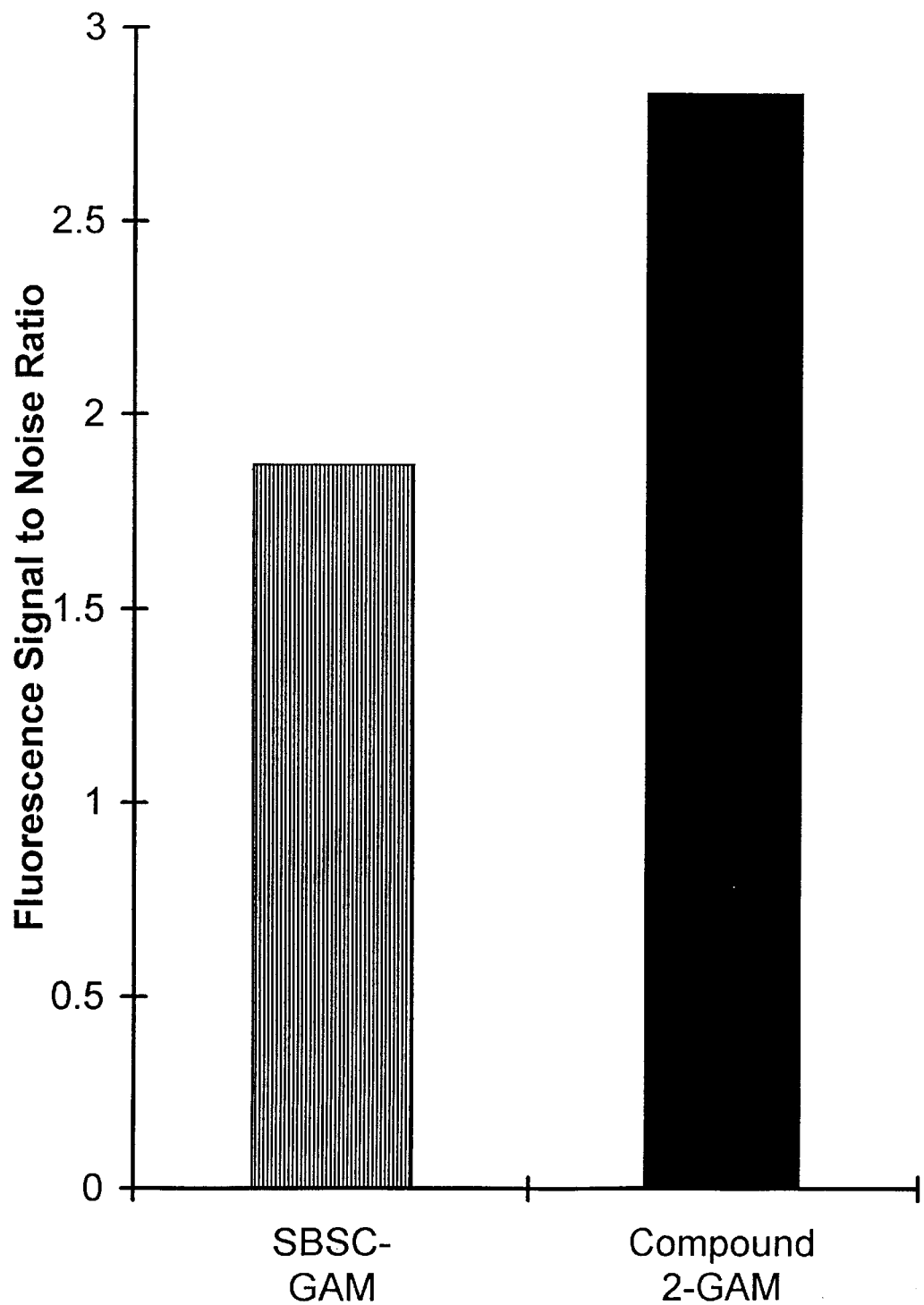
FIG. 5: A comparison of fluorescence signal-to-noise levels for cells stained with the conjugates SBSC-GAM (having a degree of substitution of 2.4) and Compound 2-GAM (having a degree of substitution of 2.8) as described in Example 12.

Comparison of staining of Jurkat cells using antibody conjugates of sulforhodamine:

A suspension of Jurkat cells are treated with anti-CD3 monoclonal antibody. The cells are stained in parallel with Compound 2-GAM (having a degree of substitution of 2.8) or SBSC-GAM (having a degree of substitution of 2.4). The cells are stained using 5 µg of the desired GAM conjugate per 500,000 Jurkat cells in a volume of 200 microliters of PBS-BSA. All incubations are performed on ice for 30 minutes, and the cells are washed twice with cold phosphate buffered saline (PBS), 1% BSA, between steps. The washed cells are then analyzed on a FACS Vantage flow cytometer. Typical results are presented in FIG. 5, showing that Jurkat cells stained with Compound 2-GAM exhibit a much higher fluorescence than the cells stained with SBSC-GAM.

Example 13

Preparation of an aminodextran conjugate of sulforhodamine:

A sample of aminodextran (50 mg) having an average molecular weight of 10,000 and derivatized with an average of 3.6 amino groups, is dissolved in 0.1M sodium bicarbonate to give a concentration of 10 mg/mL. A solution of Compound 2 in DMF having a concentration of 10 mg/mL is added to the dextran solution in an amount to give a dye/dextran ratio of 4. After stirring at room temperature, the conjugated dextrans are purified by gel filtration using SEPHADEX G-15 resin in water. The dextran solution is lyophilized, and the degree of substitution of the dextran is determined as described in Example 7. The dextran-conjugate exhibits a DOS of 1.1 dyes/10,000 daltons of dextran.

Example 14

Labeling actin in cells using a phalloidin conjugate of sulforhodamine:

Mammalian cells are grown on coverslips according to standard tissue culture procedures. After two days in culture, the growth medium is removed and the cells are rinsed twice with warm Hanks Balanced Salt Solution (HBSS; 0.14 g/L $CaCl_2$, 0.40 g/L KCl, 0.06 g/L $KH_2PO_4$, 0.10 g/L $MgCl_2 \cdot 6H_2O$, 0.10 g/L $MgSO_4 \cdot 7H_2O$, 8.0 g/L NaCl, 0.35 g/L $NaHCO_3$, 0.48 g/L $Na_2HPO_4$, 1 g/L D-glucose). Cells are then fixed in 3.7% formaldehyde diluted into EBSS for 10 minutes at room temperature. Cells are rinsed in phosphate buffered saline (PBS; 0.20 g/L KCl, 0.20 g/L $KH_2PO_4$, 8 g/L NaCl, 1.15 g/L $Na_2HPO_4$), and permeabilized in ice cold acetone for 10 minutes. The cells are then rehydrated in PBS for 10 minutes, and stained with a 165 nM solution of Compound 5 in PBS. The stained cells are then rinsed twice with PBS, mounted in the mounting medium of choice, and viewed using a standard filter set used for SBSC conjugates on a fluorescence microscope. The staining of F-actin filaments using Compound 5 is consistent with that of similar, shorter wavelength tetramethylrhodamine phalloidin conjugates.

Example 15

Labeling actin in cells using a phalloidin conjugate of sulforhodamine in conjunction with a labeled antibody:

Cells are grown, fixed and permeabilized as described in Example 14. After a 10 minutes rehydration in PBS, cells are blocked in a solution of 1% bovine serum albumin/1% normal goat serum/0.1% TWEEN-20 in PBS for 30 minutes. Monoclonal anti-tubulin antibody is diluted into the blocking buffer at a concentration of 2 µg/mL (Boehringer Mannheim, Indianapolis, Ind.) and a 100 µL volume per coverslip is incubated with the cells for 1 hour. After rinsing in PBS, fluorescein goat anti-mouse antibody is diluted to 10 µg/mL and incubated with the cells for 30 minutes. After rinsing in PBS, cells are then incubated with a 165 nM solution of Compound 5 diluted in PBS for 30 minutes. Cells are rinsed a final time in PBS, mounted in the mounting medium of choice, and viewed through either a multiband filter, or through a long-wavelength filter and a fluorescein filter with a standard fluorescence microscope. Simultaneous staining of both F-actin and tubulin filaments is consistent with staining by the individual probes.

Example 16

Preparing a DNA hybridization probe using fluorescent nucleotide conjugates:

For each labeling reaction, a microfuge tube containing about 1 µg of a ~700 bp Hind III-Bgl II fragment of the *E. coli* lacZ structural gene is heated for about 10 minutes at 95° C. to fully separate the strands. The DNA is immediately cooled on ice, to prevent the strands from reannealing. To the DNA mixture on ice is added 2 µL of a 2 mg/mL mixture of random sequence hexanucleotides, in 0.5M Tris-HCl, pH 7.2, 0.1M $MgCl_2$, 1 mM dithiothreitol; 2 µL of a dNTP labeling mixture (1 mM dATP, 1 mM dGTP, 1 mM dCTP, 0.65 mM dTTP and 0.35 mM Compound 3 (Example 3). Sterile distilled and deionized water is added to the samples to bring the total volume of each to 19 µL. A 1 µL volume of Klenow DNA polymerase (2 units/µL) is added carefully to the samples and they are mixed by pipetting up and down repeatedly. The samples are incubated for one hour at 37° C. The reaction is stopped by adding 2 µL of 0.2M EDTA, pH 8.0. The labeled DNA is precipitated by addition of 2.5 µL of 4M LiCi and 75 µL prechilled (−20° C.) 100% ethanol and mixing well. Precipitation is allowed to continue for 2 hours at −20° C. and the nucleic acid is then recovered by centrifugation at 5000 rpm in a microfuge. The pellet is washed briefly with cold 70% ethanol, then with cold 100% ethanol. The pellet is dried briefly and dissolved in 10 mM Tris-HCl, pH 8.0, 1 mM EDTA. A portion consisting of 1/10 to ½ of the sample is analyzed by gel electrophoresis on a 1% agarose minigel under standard conditions. The Compound 3-labeled dUTP gives rise to clearly visible labeled DNA products that exhibit bright red fluorescence when visualized using ultraviolet trans- or epi-illumination. The labeled DNA products are suitable for in situ hybridization experiments for the detection of RNA or DNA associated with the *E. coli* lacZ gene in cells or tissues.

Example 17

Use of a wheat germ agglutinin conjugate of sulforhodamine to identify Gram positive bacteria:

A 2 mg/mL stock solution of a wheat germ agglutinin conjugate of sulforhodamine (as prepared in Example 9) is prepared using 0.1M sodium bicarbonate at pH 8.3. A 100 µL aliquot of a bacterial suspension of either *Bacillus subtilis* or *Staphylococcus aureus* (approximately $5 \times 10^7$ cells) is centrifuged in a 0.2 µm-pore size spin filter at 2000 rpm for 1–2 minutes. The cells are then washed in 100 µL of a solution that is 0.25% bovine serum albumin and 0.15M NaCl by pipetting up and down several times. The cells are then recentrifuged as above, and resuspended in 100 µL of the BSA-saline solution. A 5.0 µL aliquot of the dye-conjugate stock solution is added, and mixed by pipetting up and down several times. The sample is then incubated for 5–15 minutes at room temperature. The stained sample is then centrifuged at 2000 rpm for 1–2 minutes to remove the staining solution, and the bacteria are resuspended in 100 μL of the BSA-saline solution. Approximately 10 μL of the suspension is transferred to a slide, a coverslip is applied and sealed, and the sample is observed immediately using a fluorescence microscope. The Gram-positive bacteria exhibit red fluorescence labeling.

Example 18

Quenching of a sulforhodamine conjugate by an anti-tetrametbylrhodamine antibody:

A solution of a streptavidin conjugate of Compound 2 is prepared that exhibits an absorbance of 0.06 at 575 nm. To this solution is added 50 μL of a 1 μg/μL solution of rabbit anti-tetramethylrhodamine antibody (Molecular Probes, Inc. Eugene Oreg.), which is known to crossreact with the sulforhodamine fluorophore. Greater than 50% of the fluorescence of the sulforhodamine fluorophores is quenched, as determined by quantitative fluorescence measurements in a SLM fluorometer.

Example 19

Binding of opsonized labeled *E. coli* to the Fc receptor of neutrophils:

Heat-killed bacteria are prepared and labeled with Compound 2 as described in Example 10. The Compound 2-labeled bacteria are then opsonized either with a 1:50 dilution of rabbit polyclonal anti-bacteria IgG, or with a 1:50 dilution of fresh human serum in PBS, (pH 7.4) at 4° C. for 30 minutes, then washed with PBS. The opsonized bacteria are incubated with human neutrophil at a ratio of 100:1 in PBS at 4° C. for 30 minutes, then at 37° C. for 30 minutes. Following washing with PBS, neutrophils are examined under a microscope to identify the phagocytosis of Compound 2-labeled bacteria. Phagocytosis is quantitated as a phagocytic index (PI), the number of phagocytosed bacteria in 100 neutrophils. Alternatively, phagocytosis is assessed by flow cytometry using the fluorescence intensity of individual Compound 2-labeled bacteria as the reference to calculate the phagocytosis index.

It is to be understood that, while the foregoing invention has been described in detail by way of illustration and example, numerous modifications, substitutions, and alterations are possible without departing from the spirit and scope of the invention as described in the following claims.

What is claimed is:

1. A dye-conjugate comprising a conjugated substance that is a peptide, protein, polysaccharide, nucleotide, oligonucleotide or nucleic acid polymer to which is attached one or more dye molecules, which may be the same or different, having the formula

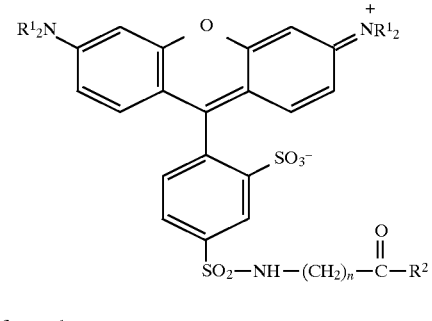

or the formula

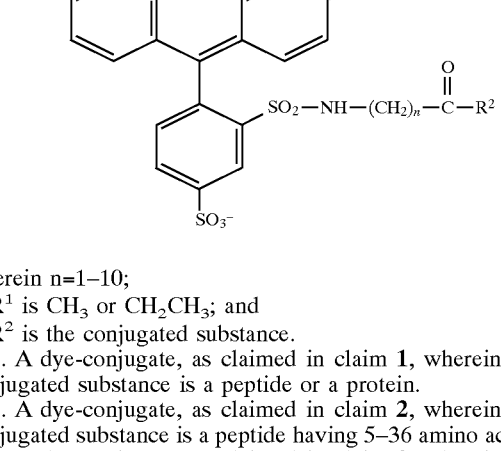

wherein n=1–10;
R$^1$ is CH$_3$ or CH$_2$CH$_3$; and
R$^2$ is the conjugated substance.

2. A dye-conjugate, as claimed in claim 1, wherein the conjugated substance is a peptide or a protein.

3. A dye-conjugate, as claimed in claim 2, wherein the conjugated substance is a peptide having 5–36 amino acids.

4. A dye-conjugate, as claimed in claim 2, wherein the conjugated substance is an antibody, a fragment of an antibody, an avidin or a streptavidin.

5. A dye-conjugate, as claimed in claim 2, wherein the conjugated substance is a lipoprotein or a glycoprotein.

6. A dye-conjugate, as claimed in claim 1, wherein the conjugated substance is a polysaccharide, a glycoprotein, the carbohydrate portion of a nucleotide, the carbohydrate portion of a nucleic acid polymer, or a periodate-oxidized ribonucleic acid.

7. A dye-conjugate, as claimed in claim 1, wherein the conjugated substance is a ribonucleotide, a deoxyribonucleotide, a dideoxyribonucleotide, an oligonucleotide or a nucleic acid polymer.

8. A dye-conjugate, as claimed in claim 7, wherein the conjugated substance is a uridine triphosphate or a deoxyuridine triphosphate.

9. A dye-conjugate, as claimed in claim 7, wherein said dye is bound to the conjugated substance at a purine or pyrimidine base through an amide, ester, ether or thioether bond.

10. A dye-conjugate, as claimed in claim 7, wherein said dye is bound to the conjugated substance via a phosphate, thiophosphate, phosphite, or phosphonate group through an ester or amide bond.

11. A dye-conjugate, as claimed in claim 1, where the conjugated substance is attached via an amide, ester or thioester linkage.

12. A dye-conjugate, as claimed in claim 1, wherein n=3–5.

13. A method of detecting a complementary member of a specific binding pair in a sample, comprising:
 a) adding to said sample a dye-conjugate of a first member of a specific binding pair for which there is a complementary member, to which is attached one or more dye molecules, which may be the same or different, having the formula

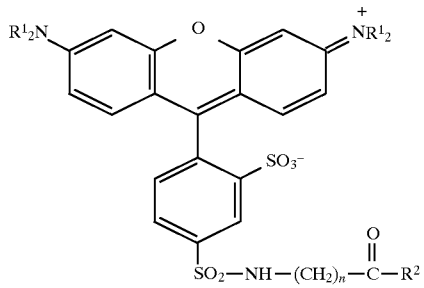

or the formula

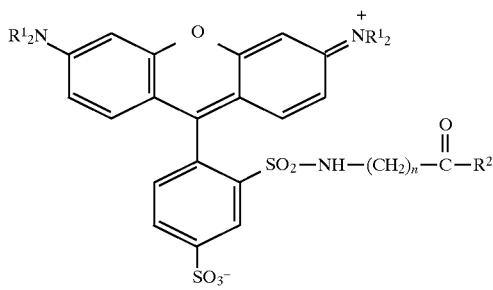

wherein n=1–10;
$R^1$ is $CH_3$ or $CH_2CH_3$; and
$R^2$ is the first member of the specific binding pair;
b) allowing sufficient time for the dye-conjugate to form a complex with the complementary member; and
c) detecting the complex to locate the complementary member.

14. A method, as claimed in claim 13, wherein the first member of the specific binding pair is a peptide, a protein, a nucleotide, an oligonucleotide or a polysaccharide.

15. A method, as claimed in claim 13, wherein the complex is detected by its fluorescence response.

16. A method, as claimed in claim 13, wherein the first member of the specific binding pair is an antibody, an antibody fragment, avidin, streptavidin, or a conjugate of an antibody, an antibody fragment, avidin, or streptavidin and the complementary member is a hapten, an antigen or a biotin.

17. A method, as claimed in claim 16, wherein the first member of the specific binding pair is avidin or streptavidin or a conjugate of avidin or streptavidin.

18. A method, as claimed in claim 16, wherein the first member of the specific binding pair is an antibody or antibody fragment or a conjugate of an antibody or an antibody fragment.

19. A method, as claimed in claim 16, wherein the complementary member is a hapten having a molecular weight less than 1,000.

20. A method, as claimed in claim 19, wherein the complementary member is present in a cell, bacteria, virus or yeast cell.

21. A method, as claimed in claim 13, wherein the first member of the specific binding pair is an oligonucleotide or nucleic acid polymer.

22. A method, as claimed in claim 21, wherein the complementary member is present in a cell, bacteria, virus or yeast cell.

23. A method, as claimed in claim 21, wherein the complementary member is immobilized on a polymer, polymeric membrane or polymeric particle.

24. A method, as claimed in claim 21, wherein the complementary member is present in an electrophoretic gel.

25. A method, as claimed in claim 15, wherein the fluorescence response is detected using a flow cytometer, a fluorescence microscope, a fluorometer or a fluorescence plat reader.

26. A method, as claimed in claim 25, further comprising distinguishing the fluorescence response from that of a second fluorophore having detectably different optical properties.

27. A method, as claimed in claim 25, wherein the fluorescence response is detected using a flow cytometer, further comprising sorting said complex based on the fluorescence response.

28. A complex of a dye-conjugate of a first member of a specific binding pair and a complementary member of said complementary member, where the first member of the specific binding pair is attached to one or more dyes, which may be the same or different, having the formula

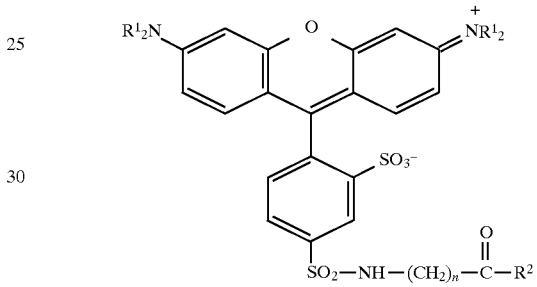

or the formula

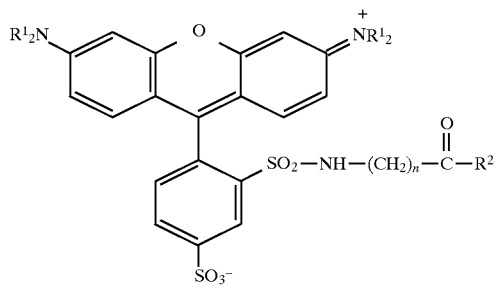

wherein n=1–10;
$R^1$ is $CH_3$ or $CH_2CH_3$; and
$R^2$ is the first member of the specific binding pair.

29. A complex, as claimed in claim 28, wherein the first member of the specific binding pair is a peptide or a protein.

30. A complex, as claimed in claim 29, wherein the first member of the specific binding pair is an antibody, toxin, lipoprotein, lectin, avidin, streptavidin, protein A or protein G.

31. A complex, as claimed in claim 28, wherein the first member of the specific binding pair is a polysaccharide.

32. A complex, as claimed in claim 28, wherein the first member of the specific binding pair is a drug or toxin.

33. A complex, as claimed in claim 28, wherein the first member of the specific binding pair is a nucleotide, oligonucleotide or a nucleic acid polymer.

34. A dye-conjugate, prepared by the reaction of a substance that is a peptide, protein, polysaccharide, nucleotide, oligonucleotide or nucleic acid polymer with a reactive dye having the formula
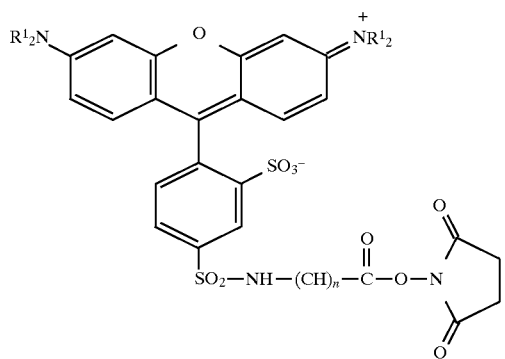
or the formula
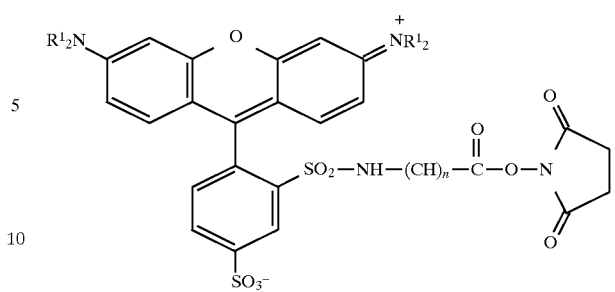
or a mixture thereof, wherein
n=1–10; and
$R^1$ is $CH_3$ or $CH_2CH_3$.
* * * * *